US009427159B2

(12) United States Patent
Chang

(10) Patent No.: US 9,427,159 B2
(45) Date of Patent: Aug. 30, 2016

(54) MEDICAL CLOUD SYSTEM WITH AN AUTOMATICALLY CHECKING AND FEEDING BACK SELF-STATUS FUNCTION

(71) Applicant: OSTAR MEDITECH CORP., New Taipei (TW)

(72) Inventor: Kuo-Yuan Chang, New Taipei (TW)

(73) Assignee: OSTAR MEDITECH CORP., New Taipei (TW)

( * ) Notice: Subject to any disclaimer, the term of this patent is extended or adjusted under 35 U.S.C. 154(b) by 364 days.

(21) Appl. No.: 14/087,234

(22) Filed: Nov. 22, 2013

(65) Prior Publication Data

US 2015/0031962 A1 Jan. 29, 2015

(30) Foreign Application Priority Data

Jul. 29, 2013 (TW) .............................. 102127166 A

(51) Int. Cl.
*A61B 5/00* (2006.01)
*G06F 19/00* (2011.01)
*A61B 5/0205* (2006.01)
*A61B 5/0402* (2006.01)
*A61B 5/145* (2006.01)
*A61B 5/01* (2006.01)

(52) U.S. Cl.
CPC .......... *A61B 5/0022* (2013.01); *G06F 19/3412* (2013.01); *A61B 5/01* (2013.01); *A61B 5/02055* (2013.01); *A61B 5/0402* (2013.01); *A61B 5/14532* (2013.01); *A61B 5/14542* (2013.01)

(58) Field of Classification Search
CPC ............. A61B 5/0022; G06F 19/3418; G06F 19/3412; H04L 67/12; H04L 67/125
See application file for complete search history.

(56) References Cited

U.S. PATENT DOCUMENTS

2013/0346108 A1* 12/2013 Kamen ............... G06F 19/3468
705/3
2015/0208921 A1* 7/2015 Kobayashi ............. G06Q 50/24
340/870.07

* cited by examiner

*Primary Examiner* — Robert N Wieland
(74) *Attorney, Agent, or Firm* — Muncy, Geissler, Olds & Lowe, P.C.

(57) ABSTRACT

A medical cloud system with an automatically checking and feeding back self-status function utilizes a database to receive and integrate a physiological information, an electronic physiological monitoring device intrinsic information, an electronic physiological monitoring device status information, an electronic physiological monitoring device error code or a miss operation information from an electronic physiological monitoring device through a smart transmitting unit. The database can notify user or manager of the electronic physiological monitoring device of arising of the electronic physiological monitoring device status information, the electronic physiological monitoring device error code or the miss operation information, and confirm the system status. The medical cloud system with an automatically checking and feeding back self-status function has the function of monitoring and long-distance transmitting to ensure the monitoring quality and prevent the serious consequence caused by fault or error of the electronic physiological monitoring device.

9 Claims, 1 Drawing Sheet

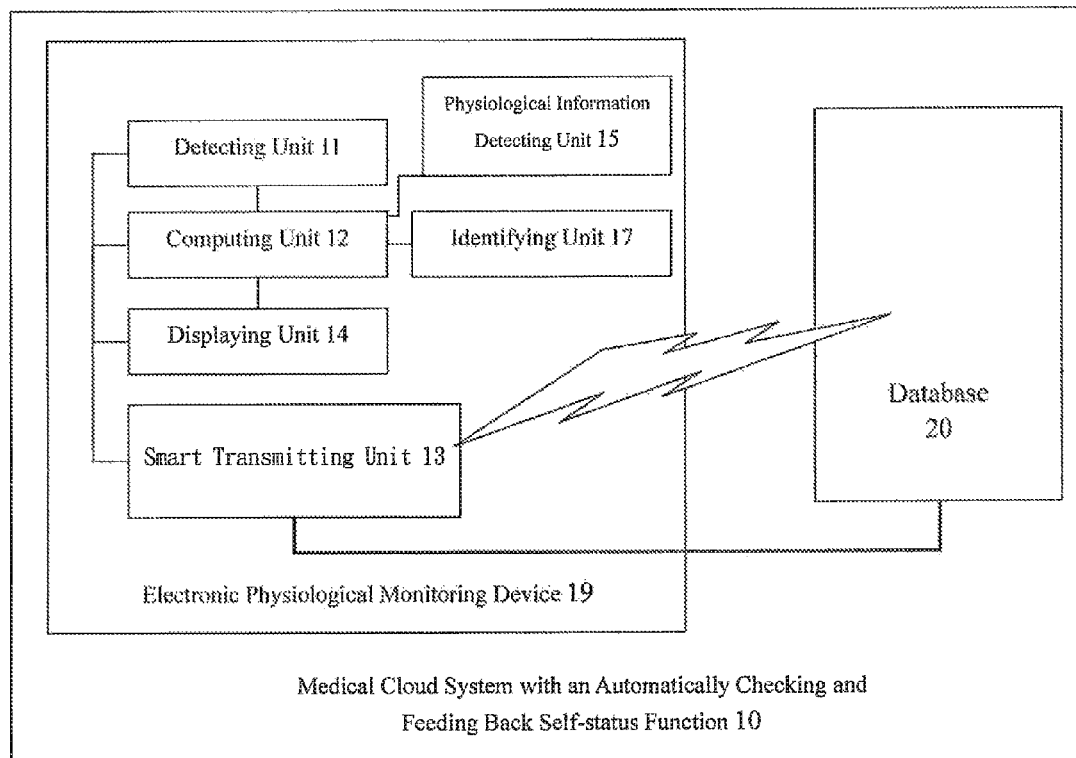

MEDICAL CLOUD SYSTEM WITH AN AUTOMATICALLY CHECKING AND FEEDING BACK SELF-STATUS FUNCTION

BACKGROUND OF THE INVENTION

1. Field of the Invention

The present invention relates to a medical cloud system with an automatically checking and feeding back self-status function, and more particularly, to a multi-functional physiological monitoring system having a database with blood pressure monitor, electrocardiogram monitor, blood sugar monitor, body temperature monitor, breath monitor, weight monitor or patient monitor.

2. Description of the Prior Art

The patients in hospital have to be monitored their essential physiological information, such as blood pressure, heartbeat, breath frequency, oxygen saturation, body temperature, electrocardiogram, urination, defecation, pain index, meal amount or infusion amount. The physiological information is written out to patients' anamneses by hand in the traditional hospitals, and the electronic anamneses are adopted in the modern hospitals coming with the electronic physiological monitoring system to automatically transmit the physiological information of patients. However, most physiological information is still observed and written out by the nursing staffs and then inputted into the computer now, and this may cause extra burden of the nursing staffs. Furthermore, the data inaccuracy caused by the busy work or the handing-over of the nursing staffs may make some errors on medicining or treating. Further, the time error between the equipments and the hospital May also cause errors on medicining or treating. After leaving the hospital, the patients equipped small electronic medical appliance module for proving the essential physiological information, such as blood pressure or heartbeat, will need a perfect physiological monitoring system for electronic distance care to coordinate with the hospital nursing system. The patients' situation can be remotely monitored by nursing staffs or families through the cloud physiological monitoring system to record patients' essential physiological information, such as a heartbeat and pulse information, a blood pressure information, an oxygen saturation information, a blood sugar information, a body temperature information, an electrocardiogram information, a weight information, a breath frequency information, a meal amount information, an infusion amount information, an urination information, a defecation information, or a pain index information. The healthy situation of the patients can be tracked everyday by the nursing staffs and transmitted to the system.

Most electronic physiological monitoring systems in the market or the patient physiological monitor in the hospitals generally have the functions of measuring, computing and displaying. When the physiological information of the patient is measured, the information can be computed and displayed. The conventional physiological monitoring systems lack the functions of recording or transmitting the equipment information, equipment status, error information or user miss operation information. It may perplex the users when the monitoring precision is deviated, the equipment time is incorrect, the equipment failed or the physiological information cannot be monitored since the error or miss operation of the users. Even more, if the users cannot nose out the error monitoring results, the patients could be delayed treating or error medicining, especially in the situation of medicining or treating according to the physiological information monitored. That may cause patients in danger or even harm the patients' life.

The conventional electronic physiological monitoring systems or the patient physiological monitors used in the hospitals with communication function generally lack of the functions for the nursing staffs, doctors, patients or users to confirm the equipment information, equipment status, error information or user miss operation information. Any situation of data lost, connection fault, deviation of the monitoring precision, equipment fault or error and miss operation by users will cause confusion and error judgment by the nursing staffs, doctors, patients and users, and furthermore may delay the medicining or treating time.

Using the blood pressure detection as example, generally speaking, the conventional physiological monitoring systems used in hospitals, clinics and tele-care centers will have time error after using a period of time or setting fault, so that the measuring time will not be identical in the same organization. For example, the patient has to take medicines on schedule according to the detection result of blood pressure, and the doctor will prescribe according to the detection result of blood pressure. If a time gap exists between the blood pressure detection system and the doctor's prescription, the doctor will possibly make wrong judgment or give wrong prescription, the patient will possibly take wrong medicine, the record of doctor's prescription will possibly earlier than the patient's detection time, the nursing staffs will possibly be confused, and the patients will possibly take hypertension medicine when his blood pressure is low. These situations will cause an awful care quality of the hospitals, and may further make the patients in danger.

Further, if the electronic blood pressure meter is located in the area having high temperature difference, such as the northeast area of China with −27° C. outdoor temperature, the circuit board in equipment will be out of shape for the high temperature difference and be bent again when entering the indoor environment, such as 18° C., and this situation will cause deviation of the monitoring precision of the electronic blood pressure meter. The circuit board of the electronic blood pressure meter will be out of shape after long time storage, and the precision of measurement of the electronic blood pressure meter will be error. When the user is at a high altitude area, the internal calibration value will be affected by the altitude difference and cause inaccuracy of measurement. The users who live in the high altitude area have to send their equipments back for further calibration to fit their environment difference. It's very inconvenient to the hospital or users who cannot confirm the precision of their blood pressure meter, and the expense, time and labor for sending equipment back for calibration always perplex the users. If the precision of equipment is deviant without any record or status feedback or the equipment has an error code with notifying the user, it may cause the situations of delayed treatment or error medicining, especially for the treatment or medicining according the physiological monitoring result, and the worst situation will harm the patient or user's life.

Since the electronic physiological monitoring device has the advantages of easy operating and carrying, it is widely used in hospitals, clinics, tele-care centers, elderly community and family care center. The conventional electronic physiological monitoring device lacks of the function of recording or transmitting the intrinsic information, the status information, the error code or the user miss operation information. When the precision of the device is deviant, the measuring time is error, the device is out of order, or the user wrongly operates the device, the electronic physiological monitoring system may be unable to monitor and may confound the user. Furthermore, when the monitoring result is in error and the user cannot become aware of this situation, it may cause the situations of delayed treatment or error medicining, especially for the treatment or medicining according the physiological monitoring result, and the worst situation will harm the patient or user's life. The patients in specific or emergent situation or the residents of the elderly community who need special nursing cannot use the conventional electronic physiological monitoring system to automatically monitor their physiological information.

SUMMARY OF THE INVENTION

It is therefore an objective of the present invention to provide a medical cloud system with an automatically checking and feeding back self-status function for hospitals, clinics, care centers, doctors, nursing staffs, patients, elders and general users can monitor the physiological information and heart situation instantaneously and can record or transmit the physiological information, the electronic physiological monitoring device intrinsic information, the electronic physiological monitoring device status information, or the electronic physiological monitoring device error code to the database. The database can notify user or manager of the electronic physiological monitoring device of arising of the electronic physiological monitoring device status information, the electronic physiological monitoring device error code or the miss operation information and confirm the intrinsic information to obtain further assistance.

It is therefore an objective of the present invention to provide a medical cloud system with an automatically checking and feeding back self-status function that the system can be used in hospitals for electronic monitoring patient's blood pressure, oxygen saturation, heartbeat, electrocardiogram, blood sugar, body temperature, weight, breath frequency, meal amount, infusion amount, urination, defecation or pain index. The functions of transmitting the electronic physiological monitoring device intrinsic information, the electronic physiological monitoring device status information, the error code, or user miss operation are utilized to instantly confirm status of the electronic physiological monitoring device and transmit the physiological information to the database.

It is therefore an objective of the present invention to provide a medical cloud system with an automatically checking and feeding back self-status function that the system can be used in long-distance care center for electronic monitoring patient's blood pressure, oxygen saturation, heartbeat, electrocardiogram, blood sugar, body temperature, weight, breath frequency, meal amount, infusion amount, urination, defecation or pain index. With the functions of transmitting the electronic physiological monitoring device intrinsic information, the electronic physiological monitoring device status information, the error code, or user miss operation information and the function of cloud computing, the hospitals and the long-distance care centers can instantaneously monitor the physiological information of the patients or elders and confirm the normal operation of the physiological monitoring device.

It is therefore an objective of the present invention to provide a medical cloud system with an automatically checking and feeding back self-status function that the system also has the function of monitoring the physiological information and the function of recording and transmitting an electronic physiological monitoring device intrinsic information, an electronic physiological monitoring device status information, an error code, or a user miss operation information to a database. The monitored physiological information, an electronic physiological monitoring device intrinsic information, an electronic physiological monitoring device status information, an error code, or a user miss operation information is transmitted to a database and processed the function of data integration, smart judgment and notification. The assistance can be properly provided to different hospitals, clinics, care centers, doctors, nursing staffs, patients, elders and general users, wherein the database can be a local database, cloud database, HIS database system of the hospitals, NIS database system, HL7 database system or general database system. If the database is a general database system, the database can be connected to and exchange information with one or more than one of HIS, NIS, HL7, emergency system, intensive care unit system or outpatient system. The medical cloud system with an automatically checking and feeding back self-status function utilizes a database to receive and integrate a monitored physiological information, an electronic physiological monitoring device intrinsic information, an electronic physiological monitoring device status information, an error code, or a user miss operation information through the smart transmitting unit. The database is capable of notifying user or manager of the electronic physiological monitoring device of arising of the electronic physiological monitoring device intrinsic information, the electronic physiological monitoring device status information, the error code, or the user miss operation information, and the electronic physiological monitoring device and the database can synchronize the time remotely. The precision of the electronic physiological monitoring device can be also remotely checked and calibrated without the special equipment in the factory or extra labor time. The status of the medical cloud system can be also automatically checked and fed back without extraneous expenses or labors and achieve the purpose of calibrating the precision of the device.

It is therefore an objective of the present invention to provide a medical cloud system with an automatically checking and feeding back self-status function that the system also has the function of monitoring the physiological information and the function of confirming an electronic physiological monitoring device intrinsic information, an electronic physiological monitoring device status information, an error code, or a user miss operation information. The monitored physiological information, an electronic physiological monitoring device intrinsic information, an electronic physiological monitoring device status information, an error code, or a user miss operation information is transmitted to a database and processed the functions of data integration, smart judgment, notification, long-distance health care and cloud smart process. The function of cloud smart process can automatically judge and handle various situations and access the cloud data. The database can be wiredly or wirelessly given system maintenance, software update or software debug to the electronic physiological monitoring device. The assistance can be properly provided to different hospitals, clinics, care centers, doctors, nursing staffs, patients, elders and general users.

It is therefore an objective of the present invention to provide a medical cloud system with an automatically checking and feeding back self-status function wherein the smart transmitting unit is designed to replace the inaccurate human writing, reduce the time of human writing of the nursing staffs and prevent the mistake in the handing-over.

For the above-mentioned purposes, one embodiment of the present invention provides a medical cloud system with an automatically checking and feeding back self-status function which comprises an electronic physiological monitoring device and a database. The database is used for receiving and integrating one or more than one of a physiological information, an electronic physiological monitoring device intrinsic information, an electronic physiological monitoring device status information, or an electronic physiological monitoring device error code from the electronic physiological monitoring device. The electronic physiological monitoring device comprises: a detecting unit, for detecting one or more than one of the electronic physiological monitoring device intrinsic information, the electronic physiological monitoring device status information, or the electronic physiological monitoring device error code; a physiological information detecting unit, for detecting a physiological information, wherein the physiological information comprises one or more than one of a heartbeat and pulse information, a blood pressure information, an oxygen saturation information, a blood sugar information, a body temperature information, an electrocardiogram information, a weight information; a computing unit, connected to the detecting unit and the physiological information detecting unit, for computing one or more than one of the electronic physiological monitoring device intrinsic information, the electronic physiological monitoring device status information, the electronic physiological monitoring device error code, or the physiological information; and a smart transmitting unit, connected to the computing unit, the smart transmitting unit wiredly or wirelessly transmits one or more than one of the electronic physiological monitoring device intrinsic information, the electronic physiological monitoring device status information, or the electronic physiological monitoring device error code to the database.

Wherein, the electronic physiological monitoring device intrinsic information comprises one or more than one of an electronic physiological monitoring device identity (ID) information, a power-on time, a power-off time, a physiological monitoring time, or an electronic physiological monitoring device operation status time.

Wherein, the electronic physiological monitoring device is capable of processing a self-test procedure at power-on, in physiological monitoring period or specific time period, and transmitting the electronic physiological monitoring device status information and an electronic physiological monitoring device identity (ID) information to the database through the smart transmitting unit to record and compiling statistics of the operation status of the electronic physiological monitoring device.

Wherein, the electronic physiological monitoring device is capable of processing a self-test procedure at power-on, in physiological monitoring period or specific time period, if the electronic physiological monitoring device fails, the electronic physiological monitoring device error code and an electronic physiological monitoring device identity (ID) information will be transmitted to the database through the smart transmitting unit to record and compiling statistics of the failure status of the electronic physiological monitoring device.

Wherein, the database is capable of wiredly or wirelessly notifying user or manager of the electronic physiological monitoring device of arising of the electronic physiological monitoring device status information.

Wherein, the database is capable of wiredly or wirelessly notifying user or manager of the electronic physiological monitoring device of arising of the electronic physiological monitoring device error code.

Wherein, the database is capable of being wiredly or wirelessly given system maintenance, software update or software debug to the electronic physiological monitoring device through the smart transmitting unit.

Wherein, the electronic physiological monitoring device is capable of processing a user operation test procedure at power-on, in physiological monitoring period or specific time period, if the user has wrong posture or miss operation to cause a physiological monitoring error, the electronic physiological monitoring device will transmit an operation error code and an electronic physiological monitoring device identity (ID) information to the database through the smart transmitting unit. Wherein, the database is capable of wiredly or wirelessly notifying user or manager of the electronic physiological monitoring device of arising of the operation error code.

The medical cloud system further comprises a displaying unit connected to the computing unit for displaying one or more than one of the electronic physiological monitoring device intrinsic information, the electronic physiological monitoring device status information, the electronic physiological monitoring device error code, or the physiological information.

The medical cloud system further comprises an identifying unit, connected to the computing unit, for recording identify information of users, nursing staffs, patients or manager of the electronic physiological monitoring device.

Wherein, the electronic physiological monitoring device can monitor one or more than one of a heartbeat and pulse information, a blood pressure information, an oxygen saturation information, a blood sugar information, a body temperature information, an electrocardiogram information, a weight information, a breath frequency information, a meal amount information, an infusion amount information, an urination information, a defecation information, or a pain index information. The heartbeat and pulse information includes a heart rate information, an electrocardiogram information or a heart spectrum information. The heart spectrum information is detecting the heartbeat and pulse information of a human and transferring the heartbeat and pulse information into a spectrum. The fast Fourier transform (FFT) algorithm is used to transfer the spectrum, and the spectrum generally has 3 to 5 main frequency waveforms. The apex of the first main frequency waveform is the heartbeat frequency of a human. If some noisy waveforms appear beside the main frequency waveform, the heartbeat of the patient is an irregular situation and will be treated as abnormal. So that the heart spectrum information can be used for determining the situation of a patient's heart. The related technology is also disclosed in the TW 1280119 patent filed by the same inventor of the present application and will not be repeated again here.

Wherein, the smart transmitting unit is a wired transmission interface, such as the universal serial bus (USB) or RS232 port, or a wireless transmission interface, such as 2.4G or WiFi transmission interface.

Wherein, the medical cloud system with an automatically checking and feeding back self-status function can be connected to an ID scanner, such as a bar-code scanner, a card reader, a RFID reader or a Near Field Communication (NFC) device.

Wherein, the medical cloud system with an automatically checking and feeding back self-status function can automatically notify related person of arising of one or more than one of the electronic physiological monitoring device intrinsic information, the electronic physiological monitoring device status information, the error code, or the user miss operation information through email, SMS message, MMS message, wired transmission or wireless transmission.

Wherein, the computing unit can automatically encrypt the information while transmitting through the smart transmitting unit to prevent betraying confidential information. Wherein, the database can automatically encrypt the information after receiving it to prevent betraying confidential information. Wherein, the electronic physiological monitoring device can be used by patients in the hospital or in home. Wherein, the database can be HIS database system of the hospitals, NIS database system, HL7 database system or general database system. If the database is a general database system, the database can be connected to and exchange information with one or more than one of HIS, NIS, HL7, emergency system, intensive care unit system or outpatient system.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

FIG. 1 is a schematic diagram of the medical cloud system with an automatically checking and feeding back self-status function according to one embodiment of the present invention.

DETAILED DESCRIPTION

FIG. 1 is a schematic diagram of the medical cloud system with an automatically checking and feeding back self-status function 10 according to one embodiment of the present invention. As shown in the FIGURE, the medical cloud system with an automatically checking and feeding back self-status function 10 comprises an electronic physiological monitoring device 19 and a database 20. The database 20 is used for receiving and integrating one or more than one of a physiological information, an electronic physiological monitoring device intrinsic information, an electronic physiological monitoring device status information, or an electronic physiological monitoring device error code. The electronic physiological monitoring device 19 comprises: a detecting unit 11, for detecting one or more than one of the electronic physiological monitoring device intrinsic information, the electronic physiological monitoring device status information, or the electronic physiological monitoring device error code; a physiological information detecting unit 15, for detecting a physiological, information, wherein the physiological information comprises one or more than one of a heartbeat and pulse information, a blood pressure information, an oxygen saturation information, a blood sugar information, a body temperature information, an electrocardiogram information, a weight information; a computing unit 12, connected to the detecting unit 11 and the physiological information detecting unit 15, for computing one or more than one of the electronic physiological monitoring device intrinsic information, the electronic physiological monitoring device status information, the electronic physiological monitoring device error code, or the physiological information; and a smart transmitting unit 13, connected to the computing unit 12, the smart transmitting unit 13 wiredly or wirelessly communicated with the database 20 directly to transmit one or more than one of the electronic physiological monitoring device intrinsic information, the electronic physiological monitoring device status information, the electronic physiological monitoring device error code, or the physiological information to the database 20.

The electronic physiological monitoring device intrinsic information comprises one or more than one of an electronic physiological monitoring device identity (ID) information, a power-on time, a power-off time, a physiological monitoring time, or an electronic physiological monitoring device operation status time.

The electronic physiological monitoring device 19 is capable of processing a self-test procedure at power-on, in physiological monitoring period or specific time period, and transmitting the electronic physiological monitoring device status information and an electronic physiological monitoring device identity (ID) information to the database 20 through the smart transmitting unit 13 to record and compile statistics of the operation status of the electronic physiological monitoring device 19.

The electronic physiological monitoring device 19 is capable of processing a self-test procedure at power-on, in physiological monitoring period or specific time period, if the electronic physiological monitoring device 19 fails, the electronic physiological monitoring device error code and an electronic physiological monitoring device identity (ID) information will be transmitted to the database 20 through the smart transmitting unit 13 to record and compile statistics of the failure status of the electronic physiological monitoring device 19.

The database 20 is capable of wiredly or wirelessly notifying user or manager of the electronic physiological monitoring device 19 of arising of the electronic physiological monitoring device status information.

The database 20 is capable of wiredly or wirelessly notifying user or manager of the electronic physiological monitoring device 19 of arising of the electronic physiological monitoring device error code.

The database 20 is capable of being wiredly or wirelessly given system maintenance, software update or software debug to the electronic physiological monitoring device 19 through the smart transmitting unit 13.

The electronic physiological monitoring device 19 is capable of processing a user operation test procedure at power-on, in physiological monitoring period or specific time period, if the user has wrong posture or miss operation to cause a physiological monitoring error, the electronic physiological monitoring device 19 will transmit an operation error code and an electronic physiological monitoring device identity (ID) information to the database 20 through the smart transmitting unit 13. Furthermore, the database 20 is capable of wiredly or wirelessly notifying user or manager of the electronic physiological monitoring device 19 of arising of the operation error code.

The medical cloud system with an automatically checking and feeding back self-status function further comprises a displaying unit 14, connected to the computing unit 12 for displaying one or more than one of the electronic physiological monitoring device intrinsic information, the electronic physiological monitoring device status information, the electronic physiological monitoring device error code, or the physiological information.

The medical cloud system with an automatically checking and feeding back self-status function further comprises an identifying unit 17, connected to the computing unit 12, for recording identify information of users, nursing staffs, patients or manager of the electronic physiological monitoring device.

The electronic physiological monitoring device 19 can monitor one or more than one of a heartbeat and pulse information, a blood pressure information, an oxygen saturation information, a blood sugar information, a body temperature information, an electrocardiogram information, a weight information, a breath frequency information, a meal amount information, an infusion amount information, an urination information, a defecation information, or a pain index information. The heartbeat and pulse information includes a heart rate information, an electrocardiogram information or a heart spectrum information. The heart spectrum information is detecting the heartbeat and pulse information of a human and transferring the heartbeat and pulse information into a spectrum. The fast Fourier transform (FFT) algorithm is used to transfer the spectrum, and the spectrum generally has 3 to 5 main frequency waveforms. The apex of the first main frequency waveform is the heartbeat frequency of a human. If some noisy waveforms appear beside the main frequency waveform, the heartbeat of the patient is an irregular situation and will be treated as abnormal. So that the heart spectrum information can be used for determining the situation of a patient's heart. The related technology is also disclosed in the TW 1280119 patent filed by the same inventor of the present application and will not be repeated again here.

The smart transmitting unit 13 is a wired transmission interface, such as the universal serial bus (USB) or RS232 port, or a wireless transmission interface, such as 2.4G or WiFi transmission interface.

The medical cloud system with an automatically checking and feeding back self-status function 10 can be connected to an ID scanner, such as a bar-code scanner, a card reader, a RFID reader or a Near Field Communication (NFC) device.

The medical cloud system with an automatically checking and feeding hack self-status function 10 can automatically notify related person of arising of one or more than one of the electronic physiological monitoring device intrinsic information, the electronic physiological monitoring device status information, the electronic physiological monitoring device error code, or the user miss operation information through email, SMS message, MMS message, wired transmission or wireless transmission.

The computing unit 12 can automatically encrypt the information while transmitting through the smart transmitting unit 13 to prevent betraying confidential information. The database 20 can automatically encrypt the information after receiving it to prevent betraying confidential information. The electronic physiological monitoring device 19 can be used by patients in the hospital or in home. The database 20 can be HIS database system of the hospitals, NIS database system, HL7 database system or general database system. If the database 20 is a general database system, the database 20 can be connected to and exchange information with one or more than one of HIS, NIS, HL7, emergency system, intensive care unit system or outpatient system.

The power of the electronic physiological monitoring device 19 is provided by an alkaline battery set, a rechargeable battery set, a capacity, a power supply or an external electronic device.

Further, the above-mentioned medical cloud system with an automatically checking and feeding back self-status function 10 can be a single physiological monitoring system or a multi-function patient monitoring system.

The present invention adds the functions of confirming an electronic physiological monitoring device intrinsic information, an electronic physiological monitoring device status information, an electronic physiological monitoring device error code, or a miss operation information, and transmitting the monitored physiological information, an electronic physiological monitoring device intrinsic information, an electronic physiological monitoring device status information, an electronic physiological monitoring device error code, or a miss operation information to a database 20 to process the function of data integration, smart judgment, notification, long-distance health care and cloud smart processing. The present invention can be utilized to a general electronic physiological monitoring system to provide instantaneous physiological monitoring information to patients or elders need long term or timely assistance. Further, the database 20 can provide the wired or wireless transmission, such as internet, to the relative, doctor or nursing staff to track the patient's physiological information and achieve the purpose of long-distance health care.

The present invention provides a medical cloud system with an automatically checking and feeding back self-status function 10, to patients or elders need long term or timely assistance, that can rapidly and correctly judge and record an electronic physiological monitoring device intrinsic information, an electronic physiological monitoring device status information, an electronic physiological monitoring device error code, or a miss operation information, and assist the relative, long-distance care center, doctor or nursing staff. When using the medical cloud system with an automatically checking and feeding back self-status function 10 to continuously monitor the electronic physiological monitoring device intrinsic information, the electronic physiological monitoring device status information, the electronic physiological monitoring device error code, or the miss operation information, the related person can immediately handle the abnormal situation if any error found, and the system can be further given system maintenance, software update or software debug through the smart transmitting unit 13.

To sum up, the present invention provides a medical cloud system with an automatically checking and feeding back self-status function 10 having the functions of monitoring, transmitting and long-distance caring, and the additional function of confirming an electronic physiological monitoring device intrinsic information, an electronic physiological monitoring device status information, an electronic physiological monitoring device error code, or a miss operation information. The system can provide proper assistance to patients and elders with various requirements.

Those skilled in the art will readily observe that numerous modifications and alterations of the device and method may be made while retaining the teachings of the invention.

What is claimed is:

1. A medical cloud system with an automatically checking and feeding back self-status function, comprising an electronic physiological monitoring device and a database, the database is used for receiving and integrating a physiological information, an electronic physiological monitoring device intrinsic information, an electronic physiological monitoring device status information, and an electronic physiological monitoring device error code from the electronic physiological monitoring device, wherein the electronic physiological monitoring device comprises:

a detecting unit, for detecting the electronic physiological monitoring device intrinsic information, the electronic physiological monitoring device status information, and the electronic physiological monitoring device error code, wherein the electronic physiological monitoring device intrinsic information comprises an electronic physiological monitoring device identity (ID) information;

a physiological information detecting unit, for detecting the physiological information, wherein the physiological information comprises one or more than one of a heartbeat and pulse information, a blood pressure information, an oxygen saturation information, a blood sugar information, a body temperature information, an electrocardiogram information, a weight information;

a computing unit, connected to the detecting unit and the physiological information detecting unit, for computing the electronic physiological monitoring device intrinsic information, the electronic physiological monitoring device status information, the electronic physiological monitoring device error code, and the physiological information; and a smart transmitting unit, connected to the computing unit, the smart transmitting unit wiredly or wirelessly communicated with the database directly to transmit the electronic physiological monitoring device intrinsic information, the electronic physiological monitoring device status information, the electronic physiological monitoring device error code, and the physiological information to the database, wherein the electronic physiological monitoring device is capable of processing a self-test procedure in physiological monitoring period and transmitting the electronic physiological monitoring device status information and the electronic physiological monitoring device identity (ID) information to the database through the smart transmitting unit to record and compile statistics of the operation status of the electronic physiological monitoring device, and if the electronic physiological monitoring device fails, the electronic physiological monitoring device error code and the electronic physiological monitoring device identity (ID) information will be transmitted to the database through the smart transmitting unit to record and compile statistics of the failure status of the electronic physiological monitoring device.

2. The medical cloud system with an automatically checking and feeding back self-status function of claim 1, wherein the electronic physiological monitoring device intrinsic information further comprises one or more than one of a power-on time, a power-off time, a physiological monitoring time, or an electronic physiological monitoring device operation status time.

3. The medical cloud system with an automatically checking and feeding back self-status function of claim 1, wherein the database is capable of wiredly or wirelessly notifying user or manager of the electronic physiological monitoring device of arising of the electronic physiological monitoring device status information.

4. The medical cloud system with an automatically checking and feeding back self-status function of claim 1, wherein the database is capable of wiredly or wirelessly notifying user or manager of the electronic physiological monitoring device of arising of the electronic physiological monitoring device error code.

5. The medical cloud system with an automatically checking and feeding back self-status function of claim 1, wherein the database is capable of being wiredly or wirelessly given system maintenance, software update or software debug to the electronic physiological monitoring device through the smart transmitting unit.

6. The medical cloud system with an automatically checking and feeding back self-status function of claim 1, wherein the electronic physiological monitoring device is capable of processing a user operation test procedure at power-on, in physiological monitoring period or specific time period, if the user has wrong posture or miss operation to cause a physiological monitoring error, the electronic physiological monitoring device will transmit an operation error code and an electronic physiological monitoring device identity (ID) information to the database through the smart transmitting unit.

7. The medical cloud system with an automatically checking and feeding back self-status function of claim 6, wherein the database is capable of wiredly or wirelessly notifying user or manager of the electronic physiological monitoring device of arising of the operation error code.

8. The medical cloud system with an automatically checking and feeding back self-status function of claim 1, further comprising a displaying unit connected to the computing unit for displaying one or more than one of the electronic physiological monitoring device intrinsic information, the electronic physiological monitoring device status information, the electronic physiological monitoring device error code, or the physiological information.

9. The medical cloud system with an automatically checking and feeding back self-status function of claim 1, further comprising an identifying unit, connected to the computing unit, for recording identify information of users, nursing staffs, patients or manager of the electronic physiological monitoring device.

* * * * *